Figure 1:
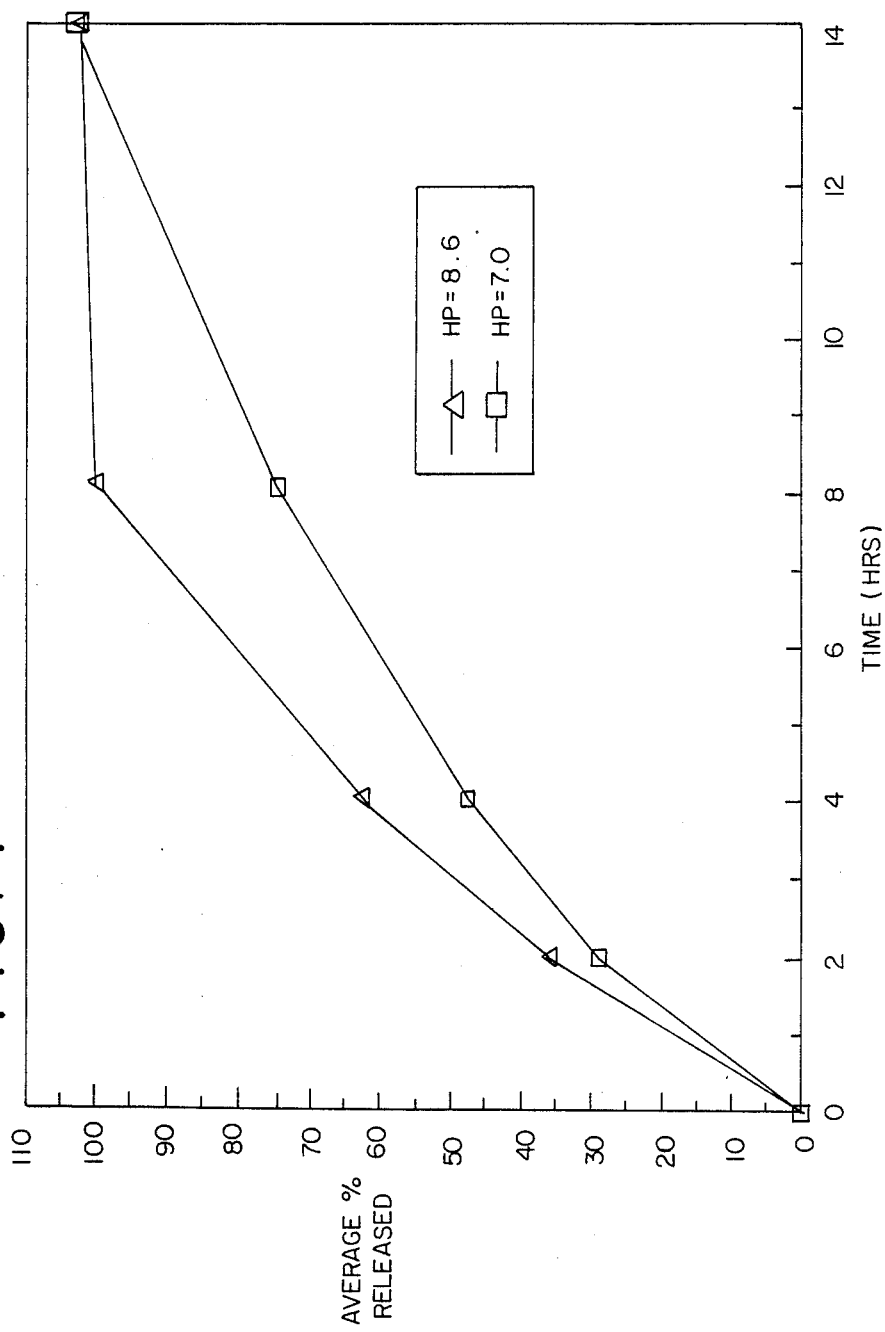

United States Patent [19]

Michelucci et al.

[11] Patent Number: 4,966,768

[45] Date of Patent: Oct. 30, 1990

[54] SUSTAINED RELEASE ETODOLAC

[75] Inventors: John J. Michelucci; Deborah M. Sherman, both of Plattsburgh; Richard J. DeNeale, Willsboro, all of N.Y.

[73] Assignee: American Home Products Corporation, New York, N.Y.

[21] Appl. No.: 268,646

[22] Filed: Nov. 7, 1988

Related U.S. Application Data

[63] Continuation of Ser. No. 100,501, Sep. 24, 1987, abandoned.

[51] Int. Cl.$^5$ .......................... A61K 9/22; A61K 9/26
[52] U.S. Cl. .................................. 424/468; 424/469; 424/470; 424/488
[58] Field of Search ................ 424/468, 469, 470, 488

[56] References Cited

U.S. PATENT DOCUMENTS

| | | | |
|---|---|---|---|
| 3,954,959 | 5/1976 | Pedersen | 424/21 |
| 4,309,404 | 1/1982 | DeNeale et al. | |
| 4,309,405 | 1/1982 | Guley et al. | |
| 4,309,406 | 1/1982 | Guley et al. | |
| 4,369,172 | 1/1983 | Schor et al. | 424/19 |
| 4,389,393 | 6/1983 | Schor et al. | 424/19 |
| 4,657,757 | 4/1987 | Hanna et al. | |

*Primary Examiner*—Shep K. Rose
*Attorney, Agent, or Firm*—John W. Routh

[57] ABSTRACT

A sustained release dosage form of etodolac is provided which is a tablet having as essential components etodolac, hydroxyproplymethylcellulose, ethylcellulose and a release rate modifying agent such as dibasic sodium phosphate, the hydroxyproplymethylcellulose having a hydroxypropoxyl content of about 7.0% to 8.6% by weight.

3 Claims, 4 Drawing Sheets

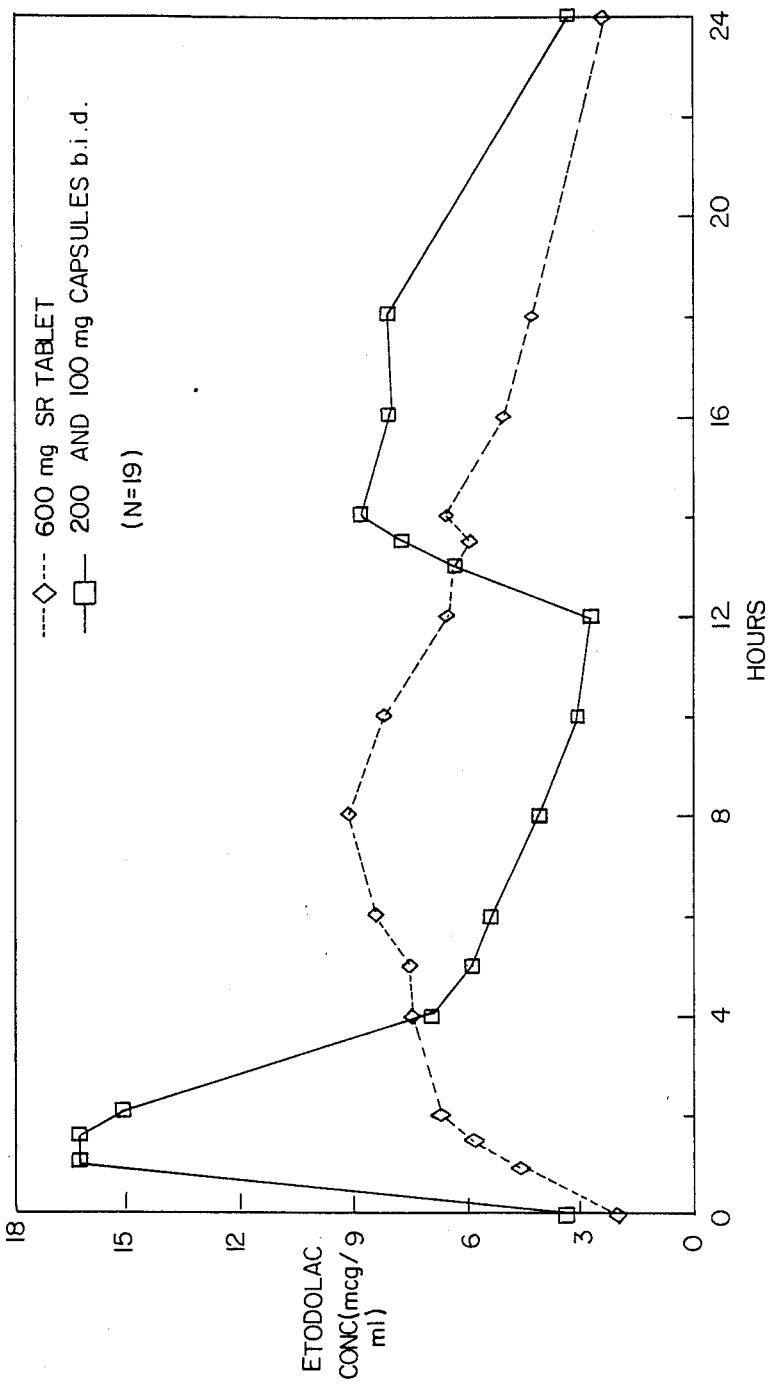

SUSTAINED RELEASE ETODOLAC

This application is a continuation of application Ser. No. 100,501, filed Sept. 24, 1987 now abandoned.

BACKGROUND OF THE INVENTION (a) Field of the Invention

This invention relates to a novel therapeutic dosage form of etodolac which provides drug plasma levels over a twenty-four hour period. More particularly, the sustained release dosage form is a tablet comprising as essential ingredients etodolac, hydroxypropylmethylcellulose, ethylcellulose and a release rate modifying agent such as dibasic sodium phosphate.

(b) Prior Art

The active agent of this invention, 1,8-diethyl-1,3,4,9-tetrahydropyrano[3,4-b] indole-1-acetic acid or a therapeutically acceptable salt thereof, is disclosed in U.S. Pat. No. 3,939,178. This active agent, hereinafter designated by its generic name, etodolac, has been reported to have analgesic and anti-inflammatory properties. It has been further reported to be active in the treatment of adjuvant arthirtis, a model of inflammatory arthritis sensitive to treatment with nonsteroidal anti-inflammatory drugs, in U.S. Pat. No. 4,533,551.

Hydroxypropylmethylcellulose alone and in combination with ethylcellulose has been proposed as an ingredient in a sustained release formulation for twenty-four hour administration or therapeutic agents. See U.S. Pat. No. 4,369,172, issued Jan. 18, 1983 which describes dosage forms as a carrier base material a particular hydroxypropylmethylcellulose, i.e. having a hydroxypropoxyl content of 9-12 weight percent, a methoxyl content of 27-30 weight percent and a number average molecular weight of less than 50,000 with up to 30% by weight of the mixture of ethylcellulose. The patent describes comparative dissolution tests run with tablets made with this carrier base material and with a carrier base material made with a hydroxypropylmethylcellulose having a hydroxypropoxyl content of 8% by weight. The dissolution tests shown in Examples 1-4 of the patent indicate that the tablets made from the 8% hydroxypropxyl content material dissolve faster and release drug more rapidly than tablets made from 10.3% hydroxpropoxyl material.

Another patent, U.S. Pat. No. 4,389,393, describes controlled release dosage forms having as a carrier base material a hydroxypropylmethylcellulose having a hydroxypropoxyl content of 4-32 weight percent, a methoxyl content of 16-24 weight percent and a number average molecular weight of at least 50,000 with up to 30% by weight of the mixture of ethyl cellulose.

U.S. Pat. No. 3,954,959 issued May 4, 1976 describes dosage forms in which the medicine is admixed with a buffer, shaped into small particles and subsequently coated with a film forming material such as ethylcellulose for diffusion of gastrointestinal juices.

Sustained action medications effective for 24 hours or once-a-day dosage present formulation problems because of the relatively short period of time they are present in the gastro-intestinal tract prior to elimination. This is especially true for medications with short half-lives (i.e. less than 6 hours) that normally would be administered in divided doses two or more times a day. The window period for medication release into the patient's system and hence into the blood stream varies from patient to patient but normally averages 10 to 12 hours. Thus after the window period of about 10-12 hours during which the drug enters the bloodstream, half of that present is metabolized every half-life and hence concentration of the drug in the blood tapers off after about 16-18 hours. Additional formulation problems are presented when the medication is one having a relatively short elimination half-life and whose solubility shows a great degree of pH dependency. Etodolac is a medicine with a half-life of about eight hours and an aqueous solubility which is very low and pH independent below pH 3. The solubility then gradually increases with rising pH up to 5 and linearly increases with increasing pH to 7. A thirty fold difference in solubility between pH 5 to 7 has been observed.

SUMMARY OF THE INVENTION

According to this invention, novel therapeutic tablet dosage forms have been formulated to provide a once-a-day dose of eotdolac. The formulation comprises etodolac and a carrier base material made from a mixture of (i) hydroxypropylmethylcellulose having a hydroxypropoxyl content of 7.0 to 8.5% weight percent, a methoxyl content of 19-24 weight percent, and a number average molecular weight of less than 50,000, (ii) from 15-28% by weight of the mixture of ethylcellulose and a release rate modifying agent such as dibasic sodium phosphate. Etodolac is water insoluble to an appreciable extent below pH 3 and the release rate modifying agent maintains the etodolac tablet environment such that the pH solubility dependency is minimized throughout the gastrointestinal tract.

The in vitro dissolution of these novel forms shows prolonged drug release profiles through 14 hours. Surprisingly, the table dosage forms of the invention dissolve faster and release drug more rapidly as the hydroxypropoxyl content increases within the range tested to about 7 to 8.6%

The in vivo evaluation of these novel dosage forms also confirm that drug plasma levels are maintained over a twenty-four hour period and are bioequivalent to a conventional dosing regimen.

DETAILS OF THE INVENTION

The etodolac useful in the invention is of pharmaceutical grade and preferably is micronized.

The hydroxypropylmethylcellulose is the U.S.P. Substitution Type 2208 having a 2% aqueous solution viscosity of 80 to 120 cps, a methoxyl content of 19-24 weight percent, and a hydroxypropyxl content of 7.0 to 8.5 weight percent. A suitable grade is available from Dow Chemical Company, Midland, Mich. and marketed under the trademark Methocel Product Grade K100LV but specifically with a hydroxypropoxyl content of 7.0-8.5 weight percent.

Ethylcellulose useful in this invention is the National Formulary or pharmaceutical grade. Suitable grades are the medium type and standard grades marketed by Dow Chemical Company, Midland, Mich., under the Ethocel trademark. Other suitable grades are those marketed by Hercules, Inc. of Wilmington, Del. and Biddle-Sawyer Corp. of New York, N.Y. Ethocel is an organo soluble ethyl ether of cellulose containing between 2.25 and 2.58 ethoxy groups per glucose unit corresponding to an ethoxy range of 45 to 49.5%.

The hydroxypropylmethylcellulose and the ethylcellulose comprise the carrier base material and the ethylcellulose content of the carrier base material can range from about 15% to about 28% by weight. The weight percent of the carrier base material in the tablet dosage forms of the invention can range from about 18% to about 30% by weight.

The release rate modifying agent is chosen so as to impart an alkaline microenvironment to the dosage form and minimize the pH solubility dependency of the etodolac as it passes through the gastrointestinal tract. The release rate modifying agent should be physiologically acceptable and can include primary, secondary or tertiary salts of phosphoric acid, or salts of phthalic acid, citric acid, tartaric acid or mixtures of such buffer salts. The preferred salt is sodium dibasic phosphate.

The following examples illustrate the formulation of the novel therapeutic tablet dosage forms of the invention. In these examples, the ethylcellulose was obtained from the Dow Chemical Company, Midland, Mich. It was a dry material of the standard type having a viscosity designation of 4 cps and an ethoxy content of 48% to 49.5%. The hydroxypropylmethylcellulose was also obtained from the Dow Chemical Company. It also was a dry material and was the Methocel Product Grade K100LV having a hydroxypropoxyl content of 7 to 8.6 weight percent.

The carrier base material concentration in the tablet formulae (hydroxypropylmethylcellulose and ethylcellulose) ranges from 21% to 26.4% (weight by weight). The ethylcellulose to hydroxypropylmethylcellulose weight ratio in the tablet formulae ranges from 1 to 3.2 to 1 to 4.2.

EXAMPLE 1

This example illustrates the preparation of a tablet with 200 milligrams of etodolac and containing the following ingredients in the listed amounts per tablet.

| Ingredient | Milligram per Tablet |
| --- | --- |
| Etodolac, micronized | 200 mg |
| Hydroxypropyl Methylcellulose, USP | 75.0 mg |
| Dibasic Sodium Phosphate, USP | 35.0 mg |
| Lactose, NF | 18.0 mg |
| Ethylcellulose, NF | 17.5 mg |
| Magnesium Stearate, NF | 3.50 mg |
| Talc | 1.00 mg |
| Theoretical Tablet Weight | =350 mg |

METHOD OF MANUFACTURE

The etodolac together with ethylcellulose, hydroxypropylmethylcellulose, lactose, talc and the dibasic sodium phosphate is dry blended, and subsequently granulated with an alcohol, denatured 23A, and methylene chloride solvent mixture. Following wet sizing, drying and dry sizing of the granulate, it is blended with magnesium stearate. The final blend is compressed into tablets of the correct weight. Subsequently, an aqueous film coat color suspension and a gloss solution are applied to the tablets. Denatured 23A is a 100:10 blend of ethyl alcohol and acetone.

EXAMPLE 2

This example illustrates the preparation of a tablet with 300 milligrams of etodolac and containing the following ingredients in the listed amounts per tablet.

| Ingredient | Milligram per Tablet |
| --- | --- |
| Etodolac, micronized | 300.0 mg |
| Hydroxypropyl Methylcellulose, USP | 112.5 mg |

-continued

| Ingredient | Milligram per Tablet |
| --- | --- |
| Dibasic Sodium Phosphate, USP | 52.5 mg |
| Lactose, NF | 27.0 mg |
| Ethylcellulose, NF | 26.25 mg |
| Magnesium Stearate, NF | 5.25 mg |
| Talc | 1.5 mg |
| Theoretical Tablet Weight | =525 mg |

The method of manufacture was the same as that of Example 1.

EXAMPLE 3

This example illustrates the preparation of a tablet with 400 milligrams of etodolac and containing the following ingredients in the listed amounts per tablet.

| Ingredient | Milligram per Tablet |
| --- | --- |
| Etodolac, micronized | 400.0 mg |
| Hydroxypropyl Methylcellulose, USP | 150.0 mg |
| Dibasic Sodium Phosphate, USP | 70.0 mg |
| Lactose, NF | 36.0 mg |
| Ethylcellulose, NF | 35.0 mg |
| Magnesium Stearate, NF | 7.0 mg |
| Talc | 2.0 mg |
| Theoretical Tablet Weight | =700 mg |

The method of manufacture was the same as that for Example 1.

EXAMPLE 4

This example illustrates the preparation of a tablet with 600 milligrams of etodolac and containing the following ingredients in the listed amounts per tablet.

| Ingredient | Milligram per Tablet |
| --- | --- |
| Etodolac, micronized | 600.0 mg |
| Hydroxypropyl Methylcellulose, USP | 168.0 mg |
| Lactose, NF | 105.8 mg |
| Dibasic Sodium Phosphate, USP | 105.0 mg |
| Ethylcellulose, NF | 52.5 mg |
| Magnesium Stearate, NF | 15.75 mg |
| Talc | 3.0 mg |
| Theoretical Tablet Weight | =1050 mg |

The method of manufacture was the same as that for Example 1.

Instead of using alcohol and methylene chloride as the granulating liquids, other liquids such as tap water may be used instead. Example 3 was repeated using tap water as the granulating liquid with satisfactory results in all respects.

Figure 2:
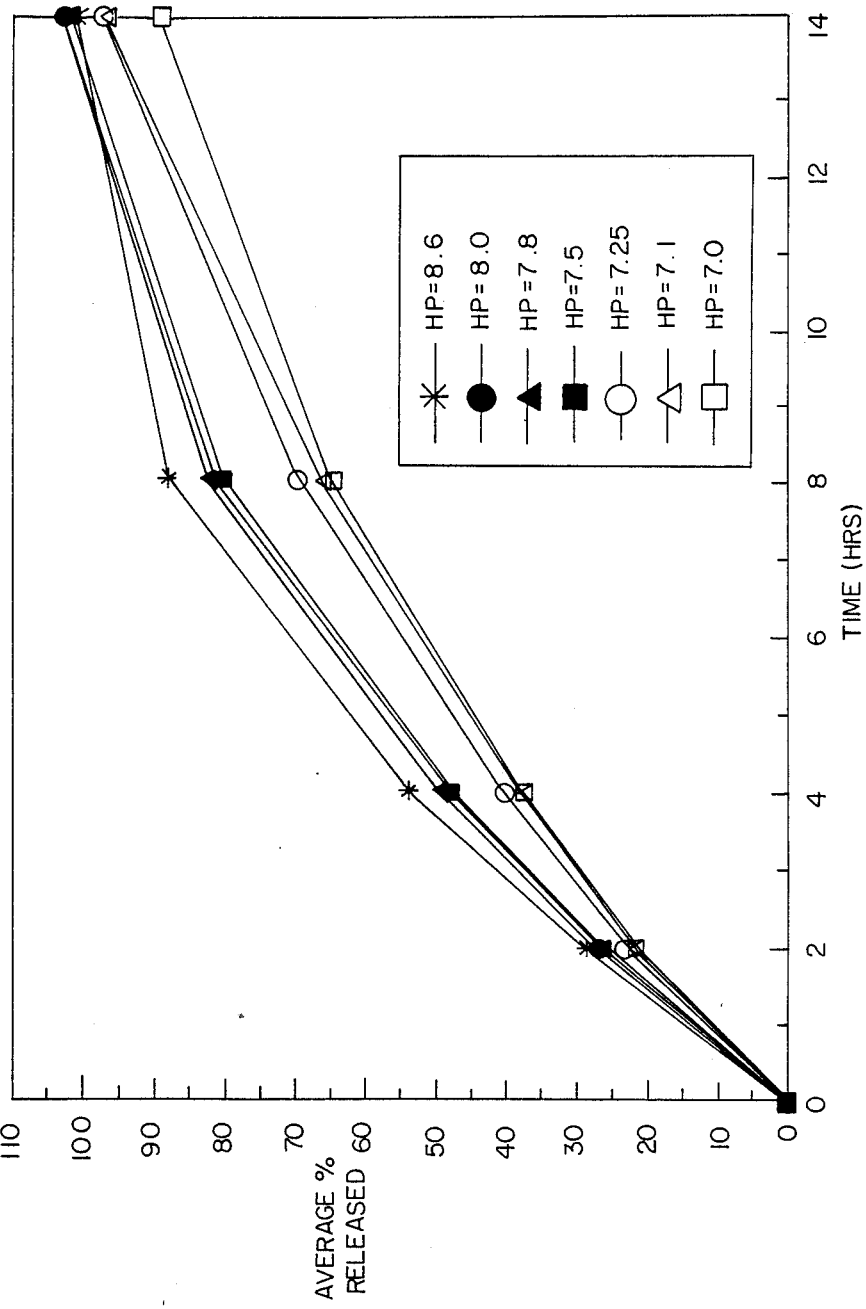
Figure 3:
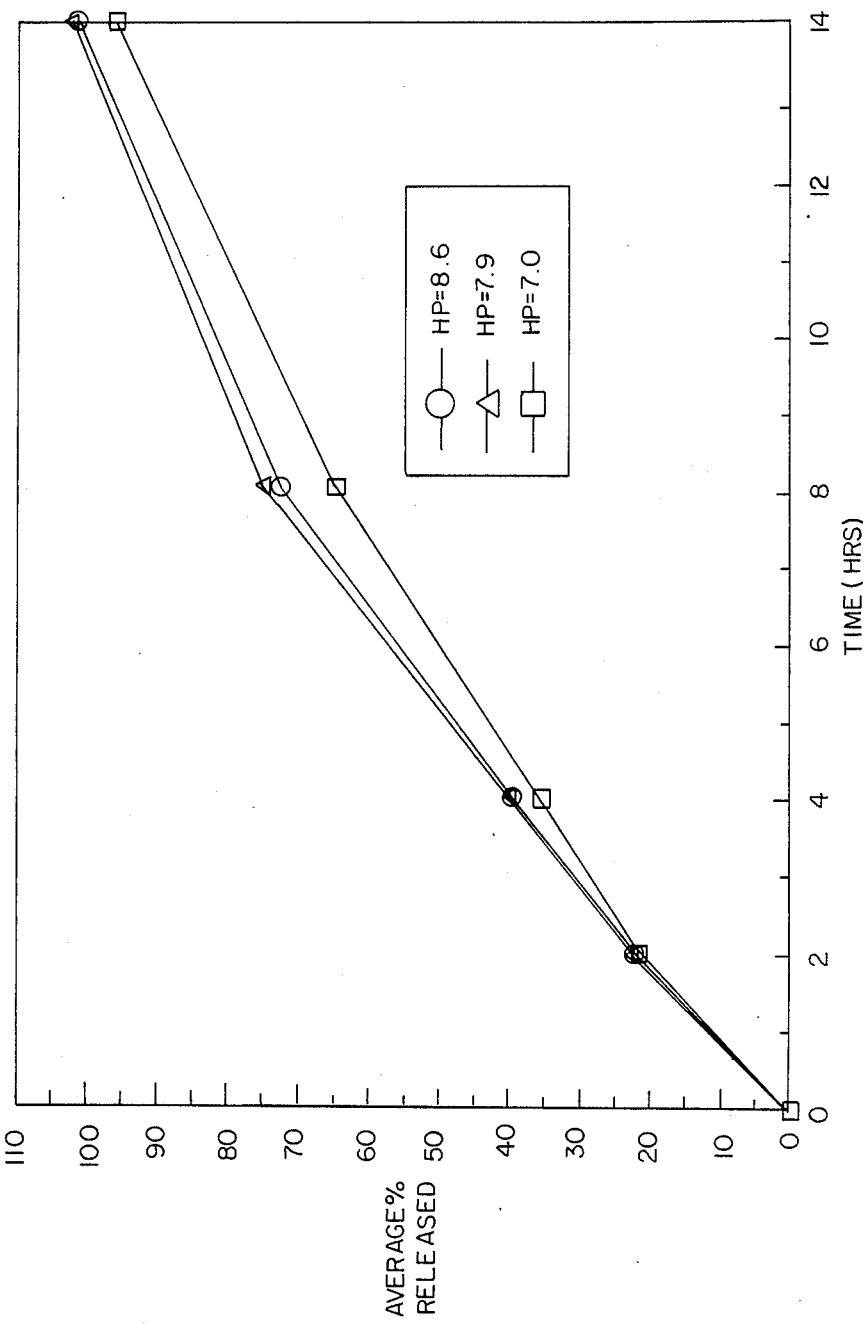

The unique dissolution profile of the novel therapeutic dosage forms of the invention is illustrated by FIGS. 1, 2 and 3 of the drawings which chart dissolution profiles of 200 400 and 600 milligram etodolac tablets (350, 700 and 1050 mg total tablet weight respectively) prepared as described in Example 1 except that the hydroxypropymethylcellulose had varying hydroxypropoxyl contents ranging from 7% and 8.6%. The dissolution data in the profiles shown in FIGS. 1, 2 and 3 establish that the tablet dosage forms of the invention dissolve faster and release drug more rapidly as the hydroxypropoxyl content increases.

The in vivo performance of the novel dosage forms of this invention has been evaluated in bioavailability studies in comparison with equivalent immediate release dosage forms. A tablet containing 600 milligrams of etodolac prepared generally according to Example 4 was given once a day and evaluated in a 3 day steady state bioavailability study in comparison with capsules containing 300 milligrams of conventional immediate release etodolac given twice a day. The 600 milligram tablet demonstrated equivalent bioavailability to its reference capsules. The pharmacokinetic parameters measured in the study are listed in Table 1 below. Comparison of the AUC (0-24) in the table for each of the 600 milligram tablet and the reference capsules shows a 90% bioavailability for the 600 milligram tablet. The $C_{max}$ and $t_{max}$ values, as would be expected, are lower and later respectively for the 600 milligram tablets. There is shown in FIG. 4 the mean etodolac plasma level for each of the 600 milligram tablets and the 300 milligram capsules administered in the bioavailability study. Each of the 600 milligram tablet and 300 milligram capsule doses showed similar average etodolac plasma levels from this study, i.e. ~6-7 mcg per milliliter.

TABLE I

RELATIVE STEADY STATE BIOAVAILABILITY AND DOSE PROPORTIONALITY OF ETODOLAC SR COMPARED TO EQUIVALENT DAILY DOSE OF IMMEDIATE RELEASE ETODOLAC

| Parameters | 300 mg b.i.d. | 600 mg S.R. |
| --- | --- | --- |
| Cmax ± SEM (mcg/mL)* | 20.84 ± 1.53 | 11.86 ± 1.08 |
| % of Reference | — | 57.2 |
| P | — | .0001 |
| AUC (0-24) ± SEM** (mcg × hr/ml) | 162.2 ± 11.7 | 146.0 ± 14.4 |
| % of Reference | — | 90.0 |
| P | — | .0222 |
| tmax ± SEM (hr)*** | 1.7 ± 0.3 | 7.8 ± 0.7 |
| % of Reference | — | 458.8 |
| P | — | .0001 |
| Cmax/Cmin ± SEM | 7.47 ± 0.86 | 7.43 ± 1.02 |
| % of Reference | — | 99.5 |
| P | — | .9388 |

*Maximum plasma concentration
**Area under plasma profile curve
***Maximum time to plasma peak

We claim:

1. A sustained release dosage form useful in providing once-a-day medication which consists essentially of an admixture of a carrier base material with etodolac and a release rate modifying agent and shaped and compressed to a solid unit dosage form having a regular and prolonged release pattern upon administration, the carrier base material comprising about 18 to 30 weight percent of the solid dosage form and being hydroxypropylmethylcellulose in admixture with 15 to 28 weight percent of the admixture of ethylcellulose, wherein the hydroxypropylmethylcellulose has a hydroxypropoxyl content of about 7.0 to about 8.6 weight percent, a methoxyl content of about 19-24 weight percent, a 2% aqueous solution viscosity of 80 to 120 cps, and an average molecular weight of less than 50,000, the release rate modifying agent being an effective amount of a physiologically acceptable buffer acid, buffer acid salt or mixture thereof.

2. The composition according to claim 1 wherein the release rate modifying agent is dibasic sodium phosphate.

3. The composition of claim 1 wherein the carrier base material is within the range of about 18% to about 30% by weight of the solid unit dosage form.

* * * * *